United States Patent [19]

Rebsdat et al.

[11] 4,123,385

[45] Oct. 31, 1978

[54] PROCESS FOR IMPROVING THE ACTIVITY OF USED SUPPORTED SILVER CATALYSTS

[75] Inventors: Siegfried Rebsdat, Burg; Sigmund Mayer, Burgkirchen, Alz; Josef Alfranseder, Marktl, Inn; Josef Riedl, Burgkirchen, Alz, all of Fed. Rep. of Germany

[73] Assignee: Hoechst Aktiengesellschaft, Frankfurt am Main, Fed. Rep. of Germany

[21] Appl. No.: 823,032

[22] Filed: Aug. 9, 1977

[30] Foreign Application Priority Data

Aug. 14, 1976 [DE] Fed. Rep. of Germany ....... 2636680

[51] Int. Cl.$^2$ .................... B01J 23/96; B01J 23/50; C07D 301/10; C07D 303/04
[52] U.S. Cl. .................................... 252/414; 252/412; 252/463; 252/477 R; 260/348.34; 422/211
[58] Field of Search ........... 252/414, 412, 420, 411 R, 252/463, 477 R; 260/348.34; 23/288 B

[56] References Cited

U.S. PATENT DOCUMENTS

| | | | |
|---|---|---|---|
| 2,831,870 | 4/1958 | McClements | 260/348.34 |
| 3,121,099 | 2/1964 | Endler | 260/348.34 |
| 4,051,068 | 9/1977 | Rebsdat et al. | 252/414 |

Primary Examiner—P. E. Konopka
Attorney, Agent, or Firm—Connolly and Hutz

[57] ABSTRACT

The activity of supported silver catalysts used up in the direct oxidation of ethylene with molecular oxygen or air is improved by impregnating the catalyst arranged in a fixed bed with a solution of a caesium and/or rubidium compound in an inert organic solvent, optionally together with up to 40% by weight of water, calculated on the total liquid, as dissolving intermediary, so as to produce a concentration gradient of from 0.3 to 20 parts of caesium and/or rubidium per 1 million parts of catalyst and per meter of fixed bed, counter to the direction of flow of the gas to be reacted. In this manner the activity of the catalyst is considerably improved which results in an increased selectivity of the oxidation of ethylene to ethylene oxide.

11 Claims, No Drawings

PROCESS FOR IMPROVING THE ACTIVITY OF USED SUPPORTED SILVER CATALYSTS

Silver catalysts, the manufacture of which has been known for a long time and is described in various patent specifications, are employed for the manufacture of ethylene oxide by the oxidation of ethylene with oxygen or air. A substantial number of large-scale industrial installations for the manufacture of ethylene oxide operate in accordance with the silver catalyst process. In this procedure, usually only a fraction of the ethylene employed is reacted. The predominant proportion of the ethylene reacted is converted, with oxygen, into ethylene oxide on the support material impregnated with silver and the remainder is virtually completely converted into carbon dioxide and water.

In the course of time, the most diverse silver catalysts have been developed, and in particular with the aim of increasing the selectivity with respect to the preferred formation of ethylene oxide and of suppressing the formation of $CO_2$ and water.

With rising prices of raw materials and increasing scarcity of raw materials, an increased selectivity of the catalysts is of particular economic importance. Thus in recent years silver catalysts, the selectivity of which for ethylene oxide is up to 75%, compared with earlier types with a selectivity of only 65 to 70%, have been successfully developed. These catalysts, such as are described, for example, in German Offenlegungsschrift No. 2,300,512, are obtained by applying to an inert support material, such as, for example, $Al_2O_3$, at the same time as the silver, 0.0004 to 0.0027 g equivalent of a potassium, rubidium or caesium compound per kg of catalyst from an aqueous solution. On the other hand, it is also known that silver catalysts lose their selectivity in the course of time, and after being used for a number of years must be replaced by new catalyst. Apart from the costs of materials, the exchange of an "exhausted" catalyst for a new one in large-scale industrial installations is extremely time-consuming and labor-intensive; in addition, it causes loss in production and high costs. Accordingly, there is the problem of whether it is possible to improve the selectivity of exhausted catalysts again by a simple treatment in order to avoid or put off for as long as possible the exchange for a new catalyst.

Such a process is described in German Auslegeschrift No. 2,519,599. In this procedure, a silver catalyst which has already been in use for a relatively long time is impregnated with a caesium nitrate and/or rubidium nitrate solution in an aliphatic alcohol containing water, and after allowing the solution to run off, the alcohol remaining on the catalyst is evaporated off at 70° to 120° C., whilst simultaneously passing nitrogen through. The selectivity of the catalyst treated in this manner is improved considerably, so that the selectivity of an unused silver catalyst is frequently achieved again.

A catalyst has now been found which has an even better selectivity than a supported silver catalyst treated according to German Auslegeschrift No. 2,519,599. It is a supported silver catalyst which has already been used for the direct oxidation of ethylene with molecular oxygen or air and which has a caesium and/or rubidium content of, on average, 10 to 1,000 part per 1 million parts (PPM) of catalyst and the particles of which are arranged in a fixed bed, characterized in that the concentration of caesium and/or rubidium on the catalyst particles increases, on average, from 0.5 to 20, preferably 1 to 15, parts per 1 million parts of catalyst and per meter of fixed bed in the longitudinal direction of the fixed bed, and the length of the fixed bed is at least 2 m.

The invention further relates to a process for improving the activity of supported silver catalysts for the direct oxidation of ethylene with oxygen or air, the catalyst being arranged as a fixed bed, by wetting a silver catalyst, which has already been used for the direct oxidation, with an impregnating liquid which contains caesium compounds and/or rubidium compounds, after which the impregnated catalyst has an average caesium and/or rubidium content of 10 to 1,000 PPM (= parts by weight per 1 million parts by weight of catalyst), characterized in that the wetting is carried out so that a concentration gradient of 0.5 to 20, preferably 1 to 15, PPM/m of caesium and/or rubidium is produced on the catalyst over at least two, preferably over 5 to 20, m of fixed bed, counter to the direction of flow of the gases to be reacted.

The period during which the catalyst, to be aftertreated, for the oxidation of ethylene to ethylene oxide was in use before the treatment according to the invention can vary from a few (about 2 to 3) weeks to several (about 6 to 10) years. It is not absolutely necessary that the activity of the catalyst has decreased, that is to say that the selectivity has decreased. However, the effect of the treatment is greater the more the catalyst has already lost its original selectivity.

The impregnating liquid should contain the caesium compounds and/or rubidium compounds in a form which is as finely divided as possible. The compounds mentioned can be present in dispersion or emulsion, but they are preferably used in the dissolved form.

Organic substances which are inert towards the catalyst are used as the solvent or liquid phase of a dispersion, and preferably those which have an average to very good volatility. For example, one or more compounds, with up to about 10 C atoms, of the following nature can be used: straight-chain, branched or cyclic, optionally aromatic hydrocarbons; ketones; carboxylic acid esters or amides or dicarboxylic acid esters or amides; primary, secondary or tertiary amines or ethers. Aliphatic, straight-chain, branched or cyclic alcohols with up to about 10 C atoms, preferably with 1 to 8 C atoms, are preferably used, and in particular those with up to 3 C atoms, such as ethanol, propanol and isopropanol. Methanol is particularly preferably employed. Mixtures of the liquids mentioned can also be used.

Up to 40% by weight, relative to the total liquid, of water can also optionally be added to these organic substances, for example in order to facilitate solution of the caesium compounds and/or rubidium compounds. However, in general purely aqueous solutions of the compounds mentioned should not be used since they have an unfavorable influence on the activity of the catalyst.

Virtually only the amount of caesium and/or rubidium applied to the catalyst, in general in the form of the corresponding cations, is decisive for the effect according to the invention.

It is of little importance with which radical (anion) caesium and/or rubidium is associated. They can be inorganic or organic radicals, especially in the form of salts, hydroxides, alcoholates and phenolates. However, this radical should not consist of substances which, in particular after treatment with the gaseous reaction mixture for the preparation of ethylene oxide at 230° to 270° C., act as a so-called "catalyst poison." Radicals (anions) suitable for the process can be, for example: sulfate, nitrite, chloride, bromide, fluoride, chlorate, bromate, cyanate, silicate, oxalate, malonate, succinate, butyrate, laurate, stearate, benzoate and phenolate.

Formates, acetates, carbonates, bicarbonates, nitrates, hydroxides or alcoholates of aliphatic alcohols with 1 to 3 C atoms are preferably employed.

Either one or more caesium compounds or rubidium compounds can be employed, and mixtures of caesium compounds and rubidium compounds are also suitable. The concentration of the caesium compounds and/or rubidium compounds is to be chosen so that 0.003 to 0.6% by weight of caesium and/or rubidium is present, relative to the total impregnating liquid. Below 0.003% by weight, the amount of the heavy alkali metals mentioned which is applied (as cations) to the catalyst is too low and above 0.6% by weight it is too high. In both cases, the increase in selectivity by the concentration gradient set up is still only slight.

In the following text, for the term "caesium and/or rubidium" the abbreviated form "heavy alkali metals" is also used, although these are not heavy metals in the customary sense. This abbreviation means alkali metals with a density of 15 and over.

The average content of caesium and/or rubidium in the silver supported catalyst after the treatment according to the invention should be 10 to about 1,000 PPM. Since this treatment aims at building up a concentration gradient, it is quite possible for individual sections of the total catalyst particles arranged as a fixed bed to have concentrations of the heavy alkali metals mentioned of lower than 10 and higher than 1,000 PPM. However, if the average value determined over the total catalyst is below 10 or above 1,000 PPM, a significant improvement in the selectivity by the process according to the invention can no longer be detected.

The concentration gradient of the compounds applied to the catalyst should be 0.5 to 20 PPM of caesium and/or rubidium per meter of the catalyst through which the gaseous reaction mixture flows, and a concentration gradient of 1 to 15 PPM/m is preferably used. The catalyst portions here with the smallest amount of applied heavy alkali metal compounds should still contain at least 1 PPM of heavy alkali metal, since an advantageous effect can no longer be detected below this concentration. Such catalyst portions unnecessarily take up a less effective space in the fixed bed.

The catalyst layer, in the fixed bed, through which the gases to be reacted flow should also be at least two meters. Below this length, virtually no improvement in the selectivity compared with the process according to German Auslegeschrift No. 2,519,599 can be detected. The upper limit of the length of the catalyst layer through which the gases flow is only set by industrial-economic considerations and can be 40 m or more. A length of 5 to 20 m is preferably chosen.

The following process is suitable for the manufacture of a supported silver catalyst which has a concentration gradient, described above, of heavy alkali metals:

Several separate portions of the used silver catalyst are wetted with impregnating liquids which have concentrations, which are different from one another and are within a range from 0.003 to 0.6% by weight (relative to this liquid), of caesium and/or rubidium in the form of at least one dissolved or dispersed chemical compound in at least one organic solvent which is inert towards the catalyst, optionally with the addition of water, each catalyst portion remaining in contact with the impregnating liquid for about 3 to 120 minutes, this liquid is then allowed to run off and the volatile constituents of the impregnating liquid which still remain on the catalyst particles are subsequently removed by warming, whilst passing an inert gas over at the same time if appropriate, after which the catalyst portions thus treated are arranged in a reactor so that the caesium and/or rubidium concentrations of the impregnating liquids with which the catalyst particles have been treated increase continuously in the direction of flow of the gases to be reacted on the catalyst.

This increase in the heavy alkali metal concentrations of the various impregnating liquids can be constant or non-constant. An approximately constant increase is appropriately chosen. Good results are achieved with a concentration increase which is 3 to 30% of the lowest concentration or of the concentration which has preceded in each case.

The upper limit of the number of catalyst portions to be treated is set only by industrial-economic considerations. In principle, the process described can be carried out on any desired plurality of catalyst portions. Preferably, 3 to 20 portions are treated with just as many impregnating liquids of varying concentration. When technical expense and effect are compared, particularly good results are achieved with 5 to 15 treated catalyst portions. These catalyst portions can differ amongst themselves in size; portions of identical size are preferably treated.

During the contact time with the impregnating liquid, the catalyst particles can be agitated, for example by stirring or turning over, in order to achieve uniform wetting.

The catalyst particles can be wetted with the impregnating liquid, for example, by spraying the liquid onto or pouring it over the particles. A procedure which has proved simple to manipulate and particularly effective is to charge a vessel with the particular catalyst portion and to fill the vessel with the impregnating liquid up to a little above the level of the catalyst particles.

Sufficient impregnating liquid should be used so that all the catalyst particles are completely wetted. There is no upper limit to the amount of impregnating liquid, from the point of view of its effect. In general, when the expense and effect are weighed against one another, favorable results are achieved with 75 to 150% by weight of impregnating liquid, relative to the catalyst to be treated.

After a treatment time of about 3 to 120 minutes, preferably 5 to 20 minutes, the impregnating liquid is allowed to run off and the catalyst particles are allowed to drain. The running off of the liquid can be accelerated, for example by pumping or applying excess pressure.

After the particles have drained, the volatile constituents of the impregnating liquid are removed by warming, if appropriate whilst simultaneously passing an inert gas over the particles. Inert gases which are used are appropriately nonflammable gases which do not promote combustion, such as nitrogen or carbon dioxide. As long as sources of ignition are eliminated and/or a large excess of the gas is used, which does not form flammable mixtures with the volatile substances, other gases, in particular air, can also be used.

Warming is not absolutely necessary during removal of highly volatile substances, but is is advisable in order to accelerate the drying operation. The temperatures applied appropriately depend on the substances to be evaporated and are about 50° to 150° C., preferably 70° to 120° C., it also being possible to apply reduced pressure for gentle drying and acceleration of the drying operation.

After the drying has ended, the individual catalyst portions are arranged in the longitudinal direction of a fixed bed, for example of a tube, in order of increasing concentration of the impregnating liquids with which these portions have been treated. The fixed bed is employed for the oxidation of ethylene with molecular oxygen or air in such a way that the fresh mixture of gases entering first comes into contact with the catalyst particles which have been treated with the lowest heavy alkali metal concentration of the impregnating liquid. The direction of flow of the gas and the heavy alkali metal concentration gradient of the catalyst particles thus run counter to one another so that the alkali metal concentration gradient increases in the direction of flow of the gas to be reacted.

In addition to the process described, heavy alkali metal concentration gradients can also be applied by other methods to the particles of a silver supported catalyst for the oxidation of ethylene, for example by allowing a migrating liquid, described above, to flow slowly, appropriately stepwise, into a heap of catalyst particles, the amount of liquid just being sufficient to wet all the particles. However, the high concentration gradients such as are obtained with treatment of the catalyst in portions cannot be achieved using this method; by comparison, the variation range is also narrow.

Using the process according to the invention, it is possible to increase the activity of supported silver catalysts which have already been in use for some time for the oxidation of ethylene with molecular oxygen or air, which activity is characterized by the selectivity for the oxidation to ethylene oxide, to an extent which is even greater than the effect which can be achieved using the process according to German Auslegeschrift No. 2,519,599. An increase in the selectivity is also obtained in the case of catalysts which have only been in use for a few weeks and which have not lost any of their original selectivity. In view of the large amounts of ethylene oxide which are produced by the ethylene oxidation process, an increase in yield of only a few percent, and even only of a few tenths of a percent, is of considerable economic importance. The process according to the invention can be carried out with commercially available catalysts in customary production installations without a significant additional expenditure on energy, investments and material. The ethylene oxide prepared shows no kind of losses in quality.

The invention is illustrated in the following text by means of Examples. The Examples and Comparison Experiments are carried out in a 10 m long tube of 40 mm diameter. The tube has a double-wall jacket in which a heat transfer medium is circulated, and the reaction temperature in the tube is thereby kept constant. The tube is completely filled with the catalyst to be investigated. The reaction gases consist of: 30% by volume of ethylene, 7% by volume of oxygen, 5% by volume of carbon dioxide and 58% by volume of methane. 0.0003% by volume (relative to the mixture) of vinyl chloride is added to this mixture as an inhibitor. These gases are passed through the vertical tube, over the catalyst, from the top downwards under a pressure of 15 bars. The space/time rate is:

$$3{,}500 \frac{\text{parts by volume of gas}}{\text{hours} \times \text{parts by volume of catalyst}} \ (\text{hour}^{-1})$$

In order to compare the activity of the individual catalysts, the temperature of the heat transfer medium is adjusted to give an ethylene conversion of 5%. The concentration of carbon dioxide and ethylene oxide in the reaction gas which leaves the tube is measured by gas chromatography, and from this the selectivity and conversion are calculated. The selectivity is to be understood as the proportion of ethylene, in percent, which is converted to ethylene oxide. The activity of a catalyst is greater the lower the temperature of the heat transfer medium required to achieve a 5% ethylene conversion and the higher the selectivity.

The catalyst employed for the experiments is a commercially available supported silver catalyst for the direct oxidation of ethylene and consists of 10.5% of silver on α-aluminum oxide as the support material. The catalyst consists of annular bodies of 8 mm length which have an external diameter of 8 mm and an internal diameter of 2 mm. The silver is distributed on the surface of the support as a discrete, spherical structure. The diameters of the silver particles are between 1 and 3μ. The support material has a specific surface area of 0.1 to 0.5 m$^2$/g.

After a treatment with rubidium compounds and/or caesium compounds, the average content of rubidium and/or caesium in the catalyst and the approximate concentration gradient present are determined by means of atomic absorption spectroscopy. (See the monograph: "Atomabsorptionsspektroskopie" ("Atomic Absorption Sepctroscopy"), Bernhard Wells Verlag Chemie 1972, page 114 et seq.). The determination is carried out in an air/acetylene flame and the atomic absorption is measured in the emission spectrum.

Each of the catalysts, which are treated with heavy alkali metal compounds and are described in more detail in the following text, is used for 200 hours for the oxidation of ethylene with molecular oxygen. As a rule, constant measurement values have been established after this time.

For reasons of clarity, the experimental conditions and experimental results are summarised in tables.

Comparison Experiment A

The commercially available silver catalyst described above is used, without further treatment with heavy alkali metal compounds, for 3 weeks for the oxidation of ethylene, in the experimental arrangement described at a heat transfer medium temperature of 245° and an ethylene conversion of 5%; thereafter, the experiment was discontinued. The selectivity of 68% measured initially did not alter during the entire period of the experiment.

Comparison Experiments B and C

A catalyst used for 3 weeks according to Comparison Experiment A is removed from the experimental tube and put into an impregnating solution, which contains the heavy alkali metal compounds, for 1 hour; the solution is then allowed to run off and the catalyst is dried. The catalyst thus treated is filled into the tube again and employed for the ethylene oxidation. For the values determined, see Table II.

EXAMPLES 1 to 11

A catalyst previously used according to Comparison Experiment A is again used. In each of the Examples, this catalyst is divided into ten equal portions and these portions are treated with impregnating solutions having a decreasing concentration of heavy alkali metal compounds. After the impregnating solution has been allowed to run off, the various catalyst portions are dried in a vacuum drying cabinet at the temperature which can be seen from Table II. The content of heavy alkali metal in each catalyst portion is determined, as described above, and the average concentration gradient and the average heavy alkali metal content are calculated. The values thus determined are given in Table I which follows.

tube thus filled is used for the oxidation of ethylene. The values determined are given in Table II.

COMPARISON EXPERIMENT D

For this experiment, a commercially available supported silver catalyst as is described initially is used, without aftertreatment with heavy alkali metal compounds. As distinct from Comparison Example A, this catalyst had already been employed for 3 years in an industrial reactor and had suffered a loss in activity in this period. (For the selectivity compared with Experiment A see Table II.)

EXAMPLE 12

The catalyst, employed in Comparison Experiment D, which had already been in use for 3 years, is treated Table I

| Example No. | Portion No. | 1 | 2 | 3 | 4 | 5 | 6 | 7 | 8 | 9 | 10 | Average Cs and/or Rb concentration in the catalyst (PPM) | Average Cs and/or Rb concentration gradient PPM/m |
|---|---|---|---|---|---|---|---|---|---|---|---|---|---|
| 1 – 6 | Rb+Cs or Cs concentration in the solution (PPM)$^x$ | 70 | 82 | 95 | 108 | 120 | 133 | 147 | 160 | 175 | 192 | | |
| | Rb+Cs or Cs concentration on the catalyst (PPM) | 26.5 | 29.5 | 32.5 | 35.5 | 38.5 | 41.5 | 44.5 | 47.5 | 50.5 | 53.5 | 40 | 3 |
| 7 | Cs concentration in the solution (PPM)$^x$ | 270 | 293 | 318 | 345 | 372 | 400 | 430 | 460 | 490 | 520 | | |
| | Cs concentration on the catalyst (PPM) | 67 | 71 | 75 | 79 | 83 | 87 | 91 | 95 | 99 | 103 | 85 | 4 |
| 8 and 9 | Cs or Rb concentration in the solution (PPM)$^x$ | 295 | 315 | 335 | 355 | 375 | 397 | 418 | 440 | 462 | 485 | | |
| | Cs or Rb concentration on the catalyst (PPM) | 71.5 | 74.5 | 77.5 | 80.5 | 83.5 | 86.5 | 89.5 | 92.5 | 95.5 | 98.5 | 85 | 3 |
| 10 | Cs concentration in the solution (TPM)$^x$ | 215 | 250 | 287 | 325 | 365 | 408 | 450 | 498 | 543 | 590 | | |
| | Cs concentration on the catalyst (PPM) | 58 | 64 | 70 | 76 | 82 | 88 | 94 | 100 | 106 | 112 | 85 | 6 |
| 11 | Cs concentration in the solution (TPM)$^x$ | 125 | 173 | 225 | 288 | 350 | 423 | 495 | 573 | 650 | 738 | | |
| | Cs concentration on the catalyst (PPM) | 40 | 50 | 60 | 70 | 80 | 90 | 100 | 110 | 120 | 130 | 85 | 10 |

$^x)$PPM = 1 part by weight per 1 million parts by weight of solution. (1 PPM = 0.0001% by weight)

The catalyst portions are filled into the reaction tube in the order of decreasing heavy alkali metal concentration, so that the highest heavy alkali metal concentration is at the bottom and the lowest is at the top, and the with a heavy alkali metal compound as described in Example 8 and thereafter employed for the oxidation of ethylene. For the values determined see Table II.

Table II

| Example No. | Cs/Rb in the impregnating solution [PPM] | Solvent | H$_2$O added [% by weight] | Cs/Rb compound | Treatment time 1) [minutes] | Dry temperature [° C] | Average Cs/Rb concentration in the catalyst [PPM] | Concentration $\left[\dfrac{PPM}{m}\right]$ | Selectivity 2) [%] | Heat transfer medium temperature 3) [° C] |
|---|---|---|---|---|---|---|---|---|---|---|
| A | — | — | — | — | — | — | — | — | 68 | 255 |
| B | 125 | CH$_3$OH | 2 | CsNO$_3$ | 60 | 100 | 40 | 0 | 74.6 | 244 |
| C | 390 | CH$_3$OH | 2 | CsNO$_3$ | 60 | 70 | 85 | 0 | 75.5 | 242 |
| 1 | | CH$_3$OH | 2 | Rb/CsNO$_3$ 4) | 10 | 70 | 40 | 3 | 76.1 | 238 |
| 2 | | C$_2$H$_5$OH | 3 | CsNO$_3$ | 10 | 85 | 40 | 3 | 76.9 | 233 |
| 3 | | n-C$_4$H$_9$OH | 4 | CsNO$_3$ | 10 | 130 | 40 | 3 | 77.0 | 232 |
| 4 | | CH$_3$OH | — | Cs$_2$CO$_3$ | 10 | 70 | 40 | 3 | 76.6 | 235 |
| 5 | Impregnation in portions, see the preceding Table I | CH$_3$OH | — | CsOOCCH$_3$ | 10 | 70 | 40 | 3 | 77.2 | 232 |
| 6 | | CH$_3$OH | — | CsOH | 10 | 70 | 40 | 3 | 77.2 | 232 |
| 7 | | CH$_3$OH | 2 | CsNO$_3$ | 10 | 70 | 85 | 4 | 78.2 | 228 |
| 8 | | CH$_3$OH | 2 | CsNO$_3$ | 10 | 70 | 85 | 3 | 77.6 | 230 |
| 9 | | CH$_3$OH | 2 | RbNO$_3$ | 10 | 70 | 85 | 3 | 73.5 | 245 |

Table II-continued

| Example No. | Cs/Rb in the impregnating solution [PPM] | Solvent | H$_2$O added [% by weight] | Cs/Rb compound | Treatment time 1) [minutes] | Dry temperature [°C] | Average Cs/Rb concentration in the catalyst [PPM] | Concentration [PPM/m] | Selectivity 2) [%] | Heat transfer medium temperature 3) [°C] |
|---|---|---|---|---|---|---|---|---|---|---|
| 10 | | CH$_3$OH | 2 | CsNO$_3$ | 10 | 70 | 85 | 6 | 77.5 | 230 |
| 11 | | CH$_3$OH | 2 | CsNO$_3$ | 10 | 70 | 85 | 10 | 77.2 | 230 |
| 12 | | CH$_3$OH | 2 | CsNO$_3$ | 10 | 70 | 85 | 3 | 77.6 | 237 |
| D | — | — | — | — | — | | | | 64 | 265 |

1) Time during which the impregnating solution acts in the stationary state on the catalyst
2) with an ethylene conversion of 5%
3) the heat transfer medium temperature required to achieve 5% ethylene conversion
4) molar ratio 1:1
5) relative to the total impregnating solution

We claim:

1. Process for improving the activity of supported silver catalysts for the direct oxidation of ethylene with molecular oxygen or air, the catalyst being arranged as a fixed bed, by applying an average caesium and/or rubidium content of 20 to 1.000 parts per 1 million parts of catalyst to the catalyst, which has already been used for the direct oxidation, with an impregnating liquid which contains caesium compounds and/or rubidium compounds, wherein the application is carried out so that a concentration gradient from 0.5 to 20 parts of caesium and/or rubidium per 1 million parts of catalyst per meter of fixed bed is produced, so that the concentration gradient increases in the direction of flow of the gases to be reacted.

2. Process according to claim 1, wherein several separate portions of the silver catalyst are wetted with impregnating liquids which have concentrations, which are different from one another, within a range from 0.003 to 0.6% by weight relative to the total impregnating liquid of caesium and/or rubidium in the form of at least one dissolved or dispersed chemical compound in at least one organic solvent which is inert towards the catalyst, optionally with the addition of water, each catalyst portion remaining in contact with the impregnating liquid for about 3 to 120 minutes, this liquid is then allowed to run off and the volatile constituents of the impregnating liquid which still remain on the catalyst particles are subsequently removed by warming after which the catalyst portions thus treated are arranged in the reactor so that the caesium and/or rubidium concentrations increase constantly in the direction of flow of the gases to be reacted on the catalyst.

3. Process according to claim 1, wherein acetates, formates, carbonates, biocarbonates, nitrates, hydroxides or alcoholates are employed as the caesium compounds and/or rubidium compounds and aliphatic alcohols which are straight-chain or branched and have a carbon atom number of 1 to 8 are employed as the solvent, together with up to 40% by weight of water, relative to the total impregnating liquid.

4. Process according to claim 1, wherein a highly volatile aliphatic alcohol with 1 to 3 C atoms is used as the solvent.

5. Process according to claim 2, characterized in that the caesium and/or rubidium concentrations of the impregnating liquids increase, with the exception of the most dilute liquid, by 3 to 30% of the lowest concentration or of the particular preceding concentration.

6. Process according to claim 2, wherein 3 to 20 catalyst portions are treated with as many impregnating liquids of varying concentration.

7. The process according to claim 1, wherein said concentration gradient of from 1 to 15 is produced.

8. The process according to claim 4, wherein said alcohol is methanol.

9. The process according to claim 6, wherein 5 to 15 catalyst portions are treated.

10. A supported silver catalyst arranged in a fixed bed, wherein the length of the fixed bed is at least 2 meters, produced by the process according to claim 1.

* * * * *